US012810975B2

(12) United States Patent
Lambaek et al.

(10) Patent No.: US 12,810,975 B2
(45) Date of Patent: Nov. 24, 2026

(54) METHOD FOR OPERATING LABORATORY SYSTEM AND LABORATORY SYSTEM

(71) Applicant: Roche Diagnostics Operations, Inc., Indianapolis, IN (US)

(72) Inventors: Ole Lambaek, Rotkreuz (CH); Dominik Schnarwiler, Rotkreuz (CH); Bert Taeymans, Rotkeuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 156 days.

(21) Appl. No.: 18/726,309

(22) PCT Filed: Dec. 20, 2022

(86) PCT No.: PCT/EP2022/087031
§ 371 (c)(1),
(2) Date: Jul. 2, 2024

(87) PCT Pub. No.: WO2023/138863
PCT Pub. Date: Jul. 27, 2023

(65) Prior Publication Data

US 2025/0069712 A1 Feb. 27, 2025

(30) Foreign Application Priority Data

Jan. 20, 2022 (EP) .................................... 22152466

(51) Int. Cl.
*G16H 10/40* (2018.01)
*G06Q 10/0631* (2023.01)
*G06Q 10/0639* (2023.01)

(52) U.S. Cl.
CPC ....... *G16H 10/40* (2018.01); *G06Q 10/06316* (2013.01); *G06Q 10/06393* (2013.01)

(58) Field of Classification Search
CPC ............. G16H 10/40; G06Q 10/06316; G06Q 10/06393

(Continued)

(56) References Cited

U.S. PATENT DOCUMENTS 5,282,149 A * 1/1994 Grandone ........ G05B 19/41865 702/19
8,346,574 B2 * 1/2013 Chirica .................. G16H 10/40 705/2

(Continued)

FOREIGN PATENT DOCUMENTS

EP 3 843 104 6/2021
WO WO2020/106696 5/2020

OTHER PUBLICATIONS

International Search Report and Written Opinion of related PCT/EP2022/087031 mailed Mar. 20, 2023.

*Primary Examiner* — Michael Tomaszewski
(74) *Attorney, Agent, or Firm* — Taft Stettinius & Hollister LLP

(57) ABSTRACT

A method for operating a laboratory system having a plurality of sample containers; a plurality of laboratory devices to handle the sample containers, the sample containers being assigned for handling to the target device; and a control device configured to control assignment of the sample containers to the target devices; and assigning the sample containers. The assigning comprises: determining a target device workload state for each target device, the workload state being between a first range limit and a second range limit, and determined according to a metric being proportional to a resource target device state indicative of sample containers assigned to the target device, and a power of an output flow of the target device, assigning the sample containers to the target devices according to the target device (Continued)

Figure 1:
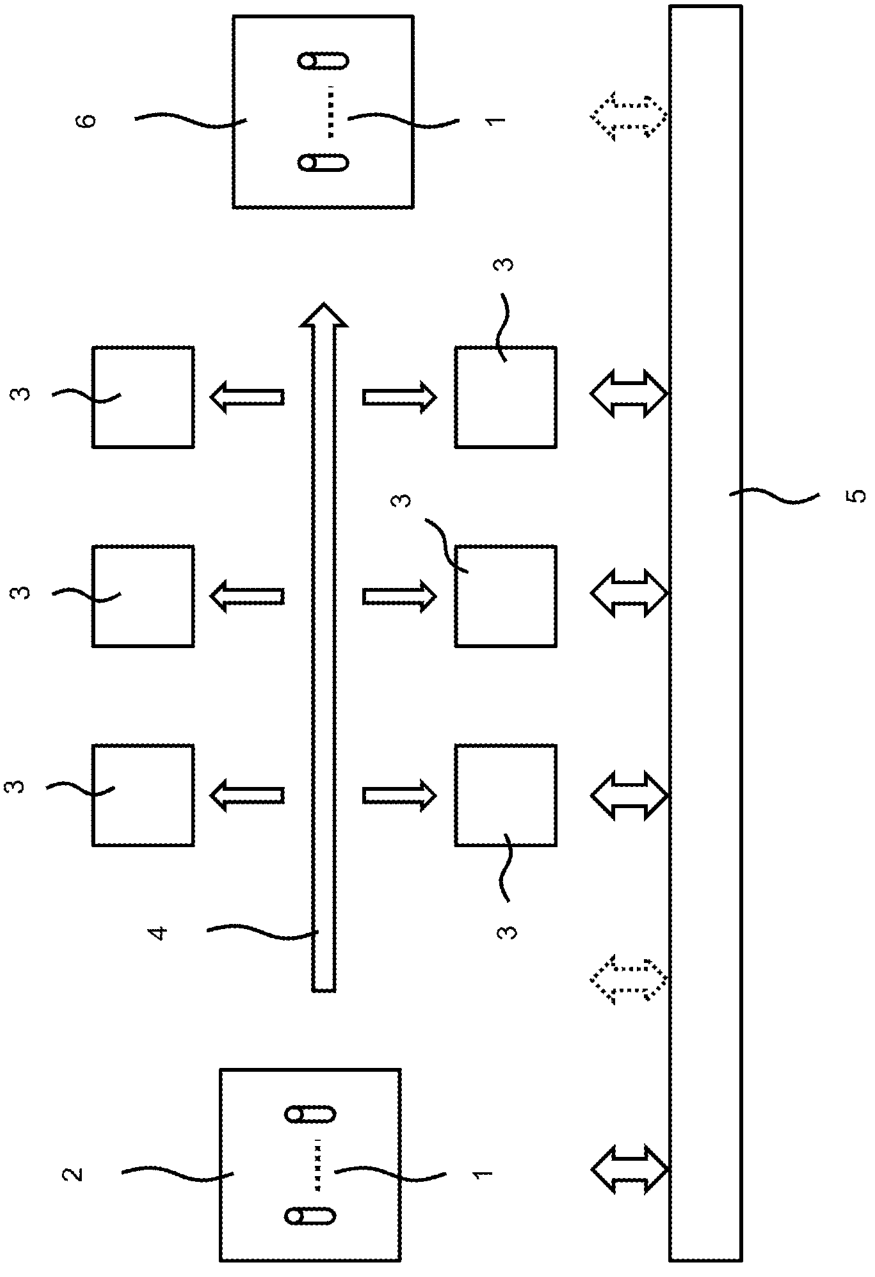

workload states; and providing the sample containers to the plurality of target devices. Furthermore, a laboratory system is provided.

13 Claims, 2 Drawing Sheets

(58) Field of Classification Search
USPC .......................................................... 705/2–3
See application file for complete search history.

(56) References Cited

U.S. PATENT DOCUMENTS 8,504,387 B1 * 8/2013 O'Meara ................ G16Z 99/00 705/2
2009/0222746 A1 * 9/2009 Chirica .................. G06Q 10/06 715/802
2012/0275885 A1 * 11/2012 Furrer .................... G01N 35/04 700/213
2013/0145299 A1 * 6/2013 Steimle .................. G16H 10/40 715/771
2014/0129172 A1 * 5/2014 Eberhardt .......... G01N 35/0092 702/108
2017/0343993 A1 * 11/2017 Vivet ................. G01N 35/0092
2020/0011888 A1 * 1/2020 Beauducel ....... G01N 35/00732
2020/0264200 A1 * 8/2020 Schofield ......... G01N 35/00732
2020/0356708 A1 * 11/2020 Kadri ...................... G06F 30/13
2020/0400697 A1 * 12/2020 Sinz ................. G01N 35/00613
2021/0132093 A1 * 5/2021 Furrer ................ G01N 35/0092
2021/0190802 A1 * 6/2021 Maetzler ................ G16H 40/20
2022/0036980 A1 * 2/2022 Beranek ........... G01N 35/00712
2023/0324423 A1 * 10/2023 Tarnawski ....... G01N 35/00871 422/50
2024/0105326 A1 * 3/2024 Baier ..................... G06Q 10/10
2024/0296921 A1 * 9/2024 Stennis .................. G16H 10/40
2025/0069712 A1 * 2/2025 Lambaek ........... G01N 35/0095

* cited by examiner

METHOD FOR OPERATING LABORATORY SYSTEM AND LABORATORY SYSTEM

The present disclosure refers to a method for operating laboratory system and a laboratory system.

BACKGROUND

A laboratory system may be provided with a plurality of laboratory devices configured to conduct at least one of pre-analysis, analysis, and post-analysis with respect to a plurality of sample containers receiving a sample to be processed in the laboratory system.

Document US 2019/0072575 A1 refers to a method for operating a laboratory system comprising laboratory instruments and a laboratory information system. A method comprises grouping laboratory instruments into instrument cluster(s) and providing a cluster manager thereto. The plurality of laboratory instruments publishes their instrument resource descriptions. Each cluster manager maintains an inventory of cluster resources and publishes a list of processing capabilities of the instrument cluster. The laboratory information system assigns processing of test order(s) to instrument clusters. Each cluster manager assigns resources of the laboratory instruments corresponding to test orders from the laboratory information system in view of the inventory of cluster resources. Each laboratory instrument carries out the processing step(s) on the biological sample as instructed by the cluster manager.

Document WO 2017/205748 A1 discloses a system and a method for load balancing specimen or sample containers between a plurality of automated detection apparatuses. The method includes: receiving a specimen container at a container pick-up station in a first automated detection apparatus; determining loading ability, transfer status, and cell availability of the first automated detection apparatus and one or more downstream automated detection apparatuses; and transferring the specimen container from the first automated detection apparatus to a downstream automated detection apparatus when a first ratio of effective available cell count to effective capacity in the first automated detection apparatus is less than a second ratio of total effective available cell count to total effective capacity of a sum of the first automated detection apparatus and the one or more downstream automated detection apparatuses.

Document EP 2 570 814 B1 refers to an automatic analysis system including devices for performing respective steps necessary for testing of specimens or samples, the automatic analysis system comprising: a transfer system providing transfer paths for the specimens which interconnect the devices, the transfer system being operable to transfer specimens along predetermined transfer routes between the devices; one or more wait regions in the devices where specimens can wait for testing or transferring; tracking unit for determining a current position of each specimen in the devices by using an order of take-in and take-out of the specimens input in the automatic analysis system, information on the predetermined transfer routes of the specimens according to details of tests to be performed on the specimens, and signals of specimen detection sensors arranged in each of the devices; a simulation unit for estimating a staying time of each specimen in one of the wait regions in the devices by simulating, based on operational models of the devices, an operation of each device in accordance with a take in/out schedule plan assuming an initial state in which each specimen is at the determined current position; and a take in/out scheduling unit for producing a final take in/out schedule by: producing an initial take in/out schedule plan for taking in or taking out an urgent specimen in preference to a normal specimen; causing the simulation unit to perform a simulation in accordance with the initial schedule plan; and, when a staying time of one of the specimens in one of the wait regions exceeds a previously set allowable staying time in the wait region concerned, correcting, in the initial take in/out schedule plan, a timing or an order of take-in and take-out of at least one of the specimens other than the specimen of which staying time exceeds the allowable staying time. Further, the following is provided: the operational models are each defined by states of a corresponding one of the devices and state transitions, the states of the device being defined by the number of specimens in each of the wait regions in the device, each state transition prescribing a transition condition, a necessary processing time, and a next state, for a corresponding one of the states of the device; and the devices include an input device. The devices include a specimen storing device which collects the specimens whose processing is completed, and an aliquoter. The operational models include an operational model for the aliquoter, and the states of the device and the state transitions defining the operational model of the aliquoter include a definition of an operation for producing a secondary specimen according to an aliquot ratio.

Document US 2014/0100139 A1 discloses a method for scheduling the order of analysis of multiple samples in a combinational clinical analyser performing a plurality of different analytical tests, the method further includes steps of: loading multiple samples in random order into a combinational clinical analyser; defining the test requirements of the multiple samples; transferring said test requirements to a flexible scheduling algorithm; and generating a schedule specifying the start times of each required test for each of said multiple samples that minimizes or maximizes a predefined objective function.

Document US 2020/0303066 A1 refers to an automated laboratory system for processing biological samples in a batch type manner. The system receives assay instructions for biological samples processing among a plurality of devices. The devices includes a pre-analytical instrument and one or more analysis systems. The system includes an orchestration core application for determining an order of performance for the assays ordered for the samples.

Document EP 1 248 170 B1 discloses a method for management of workcell systems using an automation management system to control a plurality of resources designated to handle a plurality of samples along said workcell systems to perform operations on said samples. The method comprises the following steps: associating a sample protocol to each sample; associating to each resource a resource driver, capable to drive said resource; controlling each of said resource driver by a process controller which communicates with the other resource drivers by means of variables associated to each resource, said variables defining and modifying the status of said resources; executing said sample protocols by said process controller in a concurrent way to achieve multi-threading, bottleneck avoidance, dynamic assignment of resources in mutual exclusion, sample priority handling, resource load balancing and automatic error recovery. The sample protocols are automatically controlled by re-scheduling automatic tasks on different resources according to results of the step of executing said sample protocols and the status of said resources as indicated by a status of said variables.

Document WO 2020/106 696 A1 pertains to a method for determining an optimal scheduling for an analyzer in a laboratory environment, comprising determining a load of each diagnostic analyzer amongst a plurality of diagnostic analyzers, wherein each diagnostic analyzer amongst the plurality of diagnostic analyzers may be configured to perform tasks that comprise performing a test corresponding to a discipline.

Document EP 3 843 104 A1 discloses a method to optimize an analyzer use in a laboratory having a plurality of analyzers based on laboratory workload. The method comprises determining current laboratory workload, calculating workload capability of the plurality of analyzers minus one analyzer if the current laboratory workload is below a threshold criteria and if there are two or more analyzers in the plurality of analyzers, masking one of the plurality of analyzers if the current workload is met by the plurality of analyzers minus one analyzer, proceeding with current workload, and repeating the above steps until the current laboratory workload has been completed.

Document US 2014/129 172 A1 refers to a method comprising receiving instruction data relating to a sample in a sample container. The method includes generating, by at least one processor using a workflow management layer, a process plan for the sample, and providing the process plan to a process control layer.

Document US 2017/343 993 A1 discloses a method for load balancing specimen containers between a plurality of automated detection apparatuses. The method may include receiving a specimen container at a container pick-up station in a first automated detection apparatus; determining loading ability, transfer status, and cell availability of the first automated detection apparatus and one or more downstream automated detection apparatuses; and transferring the specimen container from the first automated detection apparatus to a downstream automated detection apparatus when a first ratio of effective available cell count to effective capacity in the first automated detection apparatus is less than a second ratio of total effective available cell count to total effective capacity of a sum of the first automated detection apparatus and the one or more downstream automated detection apparatuses.

SUMMARY

It is an object of the present disclosure to provide a method for operating a laboratory system and a laboratory system which allow for more efficient handling of a plurality of sample containers within the laboratory system configured for at least one of pre-analysis and analysis of samples or specimens.

For solving the object a method for operating a laboratory system according to the independent claim 1 is provided. In addition a laboratory system according to the independent claim 11 is provided. Further embodiments are disclosed in dependent claims.

According to an aspect, a method for operating a laboratory system is provided, comprising providing a laboratory system having: a plurality of sample containers configured to contain a sample to be processed for at least one of pre-analysis and analysis in the laboratory system; a plurality of laboratory devices providing for a plurality of target devices each configured to handle one or more sample containers from the plurality of sample containers, the one or more sample containers being assigned for handling to the target device in operation of the laboratory system; and a control device configured to at least control assignment of the plurality of sample containers to the plurality of target devices. The method comprises assigning the plurality of sample containers to the plurality of target devices in operation of the laboratory system, further comprising determining a target device workload state for each of the plurality of target devices. The target device workload state is in a range between a first range limit indicative of a first capacity for handling sample containers and a second range limit indicative a second capacity for handling sample containers, the second capacity being a higher capacity than the first capacity for handling sample containers. The target device workload state is determined according to a metric being proportional to (i) a resource target device state indicative of a present number of sample containers assigned to the target device, and (ii) a power of an output flow of the target device (an output flow of the target device raised to a power, preferably of a number), the output flow being indicative of output of sample containers per time by the target device. The plurality of sample containers is assigned to the plurality of target devices according to the target device workload states; and the plurality of sample containers is provided to the plurality of target devices for handling according to the assignment.

According to another aspect, a laboratory system is provided, comprising: a plurality of sample containers configured to contain a sample; a plurality of laboratory devices providing for a plurality of target devices each configured to handle one or more sample containers from the plurality of sample containers, the one or more sample containers being assigned for handling to the target device in operation of the laboratory system; and a control device configured to at least control assignment of the plurality of sample containers to the plurality of target devices. The laboratory system is configured to process the plurality of sample containers for at least one of pre-analysis and analysis of the sample and further to assign the plurality of sample containers to the plurality of target devices in operation, comprising determining a target device workload state for each of the plurality of target devices. The target device workload state is in a range between a first range limit indicative of a first capacity for handling sample containers and a second range limit indicative a second capacity for handling sample containers, the second capacity being a higher capacity than the first capacity for handling sample containers. The target device workload state is determined according to a metric being proportional to (i) a resource target device state indicative of a pre-sent number of sample containers assigned to the target device, and (ii) a power of an output flow of the target device (an output flow of the target device raised to a power, preferably of a number), the output flow being indicative of output of sample containers per time by the target device. The laboratory system is further configured to assign the plurality of sample containers to the plurality of target devices according to the target device workload states, and provide the plurality of sample containers to the plurality of target devices for handling according to the assignment.

According to the technology, for each target device provided by a laboratory device in the laboratory system, a target device workload state is determined in operation of the laboratory system. The target device workload state assigned to an individual target device of the laboratory system is indicative of a target device capacity for handling sample or specimen containers while operating the laboratory system. The target device workload state assigned to the target device will range between a first range limit indicative of a first capacity and a second range limit indicative of a second capacity, the second capacity being a higher capacity for handling sample containers than the first capacity.

A metric is provided for determining the target device workload state which takes into account a resource target device state indicative of a present number of sample containers assigned to the target device. Such sample containers assigned to the target device may comprise sample containers which are presently handled by the target device. In addition or as an alternative, there may be one or more sample containers already assigned to the target device, but not yet being handled by the target device. Further, the metric is proportional to a power of an output flow or throughput of the target device, the output flow being indicative of output of sample containers leaving the target device per time (range or period). Thus, the output flow gives indication about the sample containers outputted by the target device over time. Based on the individual target device workload state assigned to the target devices one or more sample containers can be assigned to the target device in operation, thereby, having an assignment of the sample containers implemented which is responsive to the individual workload of the target devices of the laboratory system.

The target device workload state may be determined or provided as a numerical value which can easily be processed when the assignment of the plurality of sample containers to the plurality of target devices is conducted. The numerical value may be in a numerical value range between a first range limit and a second range limit indicative of a first capacity and a second capacity for handling sample containers, respectively. In an embodiment, the target device workload state may be assigned values as a percentage between 0 and 100 percent, where 100% means a low target device workload state ("idle"), and 0% means a high target device workload state ("busy"). This percentage may also be referred to as workload state percentage.

Data or information about the target device workload state may be received and processed by different modules or functional components of the controlling system controlling operation of the laboratory system, such modules or functional components, for example, being provided by software implementation or applications at different levels of the controlling system. For example, a software application assigned to some middleware of the controlling system may be in receipt of data or information about the target device workload state. Such data may be processed to control different operations in relation to handling the sample containers such as workflow within the laboratory system. For example, data or information about the target device workload state may be provided to and processed a transport device or system configured to transport sample containers from an original place to a target device. Transport of the sample containers by the transport system may be controlled in dependence on the target device workload state information.

The metric may be a number. Determining the target device workload state according to the metric may comprise setting the target device workload state equal to the metric (equating the target device workload state with the metric). In other words, the target device workload state may be determined according to the metric by equating the target device workload state with the metric.

The metric may be proportional to the output flow of the target device raised to the power of a weighting factor weighting the output flow of the target device for determining the target device workload state. In other words, the weighting factor may be an exponent by which the output flow is exponentiated. The weighting factor may be a positive or a negative number. The weighting factor may be at least 1 or greater than 1.

The metric may be inversely proportional to an initial resource target device state indicative of a starting number of sample containers assigned to the target device. If the present target device workload state is determined for a target device, in this embodiment, the starting number of sample containers assigned to the target device is taken into account as an initial resource target device state. The initial resource target device state may be an individual or common parameter applied for the target devices for initializing the resource target device state for the plurality of target devices. Following, starting from the initial resource target device state, the resource target device state may be determined or tracked for each target device individually. The parameter "resource target device state", starting from the initial resource target device state, may be decreased when a sample container is assigned to the target device. Starting from the initial resource target device state, the resource target device state may be increased, for example, when a sample container is handed over at a pick position or is processed by an in-situ device at the target device. Further, if a sample container is re-routed on a transportation surface from a first target device to a second target device, the resource target device state of the first target device may be increased, and the resource target device state of the second target device may be decreased accordingly.

Generally, the resource target device state may be a number. The initial resource target device state may be a number. The output flow may be a number.

The target device workload state of the target device i ($WLS_{TD\ i}$) may be determined as follows:

$$WLS_{TD\,i} = \frac{R_i}{R_{init}} \cdot (k_{SC\,i})^w \cdot 100$$

wherein $R_i$ is the resource target device state of the target device, $R_{init}$ is the initial resource target device state of the target device, and $(k_{SC\ i})^w$ is the output flow of the target device provided with the weighting factor w.

The resource target device state $R_i$ can be determined for target devices reachable by one or more sample containers. A target device is reachable if there is physically a path available, by means of the transport system, to transport the sample container from its origin to the destination (target device). If a target device is not reachable, a target device workload state of 0 may be assigned, thereby, preventing any sample container from being sent to the target device.

There may be an output flow of the target device $k_{SC\ i}$ commonly applied for (different) weighting factors w.

The output flow factor $k_{SC\ i}$ which may also be referred to as throughput factor is indicative of the sample container output or throughput at each target device of the plurality of target devices. The output flow factor $k_{SC\ i}$ weighted by means of the weighting factor w provides for weighting of a fast target device higher than a slow one and to detect slow or even failed target devices. Without taking into account the output flow, the target device workload state would purely depend on assigned sample containers or a length of the target device queue, which can result in reporting a target device to be highly attractive when it actually failed and all sample containers were re-routed away.

The method may determine an updated target device workload state for the target device in response to at least one of the following: updating the resource target device state of the target device, and recalculating output flow of the target device. For example, the resource target device state may be re-determined (updated) every time a sample container is added to and removed from a target device queue. When a sample container is added to the queue of the target device the resource target device state $R_i$ may be decreased by 1, and when a sample container is removed (processed) it may be increased by 1. A work flow may be calculated in time intervals, e.g. every minute, the aforementioned ratio between the actually processed and what was expected to be processed may be calculated.

The method may further comprise the following: providing a plurality of sub-ranges for a first range of the target device workload state for a first target device, wherein an overlapping range is provided for adjacent sub-ranges from the plurality of sub-ranges in which the adjacent sub-ranges are overlapping; determining a first target device workload state for the first target device, the first target device workload state being in a non-overlapping range of a first sub-range in which the first subrange is not overlapping with a second sub-range adjacent to the first sub-range; assigning the plurality of sample containers to the first target device according to the first target device workload state; determining a second target device workload state for the first target device, the second target device workload state being different from the first target device workload state and being in the overlapping range in which the first sub-range and the second sub-range are overlapping; continuing with assigning the plurality of sample containers to the first target device according to the first target device workload state; determining a third target device workload state for the first target device, the third target device workload state being different from both the first and the second target device workload state and being in a non-overlapping range of the second sub-range in which the first subrange and the second sub-range are not overlapping; and assigning the plurality of sample containers to the first target device according to the second target device workload state.

For one or more of the target devices a total range of a target device workload state which can be assigned to the target device is divided into a plurality of sub-ranges, wherein adjacent or neighbouring sub-ranges are overlapping in an overlapping range. If the first target device workload state is determined to be within a non-overlapping range of a first sub-range, assignment of the plurality of sample containers to the first target device is conducted according to the first target device workload state. If, at later time the second target device workload state is determined to be in the overlapping range in which the first sub-range and the second sub-range are overlapping, it is continued with assigning a plurality of sample containers to the first target device according to the first target device workload state. For example, such change of the first target device workload state may not be provided to or received by a control mechanism configured to assign the sample containers to the first target device. Thus, the control mechanism not having received information or data about the second target device workload state, will not change procedure for assignment of the plurality of sample containers to the first target device. However, if the first target device workload state for the first target device is determined or found to be no longer in the overlapping range, but in the non-overlapping range of the second sub-range, procedure for assignment of the plurality of sample containers to the first target device will change by taking into account (the value of) the third target device workload state. By having such overlapping design of the sub-ranges implemented, frequent change of the assignment (procedure) of sample containers because of amended or changed target device workload state can be avoided. Only if some change of the target device workload state goes "beyond" the overlapping range into another sub-range the newly determined target device workload state will be taken into account. The sub-ranges may also be referred to as buckets representing given or pre-determined intervals for (the value of) the target device workload state. The overlapping design of the sub-ranges can provide for a hysteresis behaviour.

The method may further comprise the following: providing first priority data indicative of a first priority for handling a first sample container from the plurality of sample containers; providing second priority data indicative of a second priority for handling the first sample container, the second priority being indicative of lower urgency for handling the first sample container in operation than the first priority; determining a first priority target device workload state for the first sample container according to the first priority; determining a second priority target device workload state for the first sample container according to the second priority; selecting one of the first priority target device workload state and the second priority target device workload state; and assigning the target device workload state selected to the first sample container. The target device workload state is determined for different priorities assigned to the first sample container. Depending on the priority there will be different target device workload state. The different priorities, for example, may refer to "normal priority" and "urgent priority" indicating normal procedure for handling a sample container within the laboratory system and urgent handling, respectively. Urgent handling (high priority) may be conducted in case analysis of a sample is urgently needed by some physician. Contrary, a sample container may be assigned "normal or routine priority" in case of absent of such urgency. In an embodiment, the different priorities assigned to some sample container may be indicative of different time limits for handling or processing the sample container by the laboratory system.

The weighting factor w supports balancing of how important the flow of sample containers at the target device is. For sample containers of high priority it is critical that an interface from the transport system to the target device is not blocked. It would be critical for the sample container of high priority (emergency) to end up in front of the target device. A sample container of high priority does not benefit from overtaking a sample container with lower priority when there is no flow of sample containers at the target device. Thus, all sample containers need to wait for processing. The target device workload state, with respect for the sample container of high priority, applies a higher value of w compared routine sample container (lower priority) which is less affected by waiting in front of the target device with low or no flow at the moment.

With respect to different priorities $prio_k$ (k=1, 2, . . . ), the target device workload state of the target device i ($WLS_{TD\ i,\ prio\ k}$) may be determined as follows:

$$WLS_{TD\,i,\,prio\,k} = \frac{R_{prio\,k,\,i}}{R_{init}} \cdot (k_{SC\,i})^{w_{prio\,k}} \cdot 100.$$

The weighting factor $w_{prio\ k}$ is going to be different for different priorities. The weighting factor can be set individually for different priorities in order to weight the output or throughput flow of sample containers $(k_{SC\ i})^{w_{prio\ k}}$ in line with the priority assigned to the sample container. Some higher weighting factor will be indicative of higher priority. There may be an output flow of the target device $k_{SC\ i}$ commonly applied for the different priorities.

$R_{prio\ k,i}$ may be initialized with $R_{init}$ being, for example, a universal parameter for each target device (TD) and all priorities (prio). $R_{prio\ k,i}$ of the target device i and priority k may be decreased when a sample container with the priority k is assigned to the target device i. $R_{prio\ k,i}$ of the target device i and priority k may be increased, for example, when a sample container with priority k is handed over at a pick position or is processed by an in-situ device at the target device. Further, if a sample container is re-routed on a transportation surface of the transport system from target device 1 to target device 2, $R_{prio\ k,1}$ may be increased, and $R_{prio\ k,2}$ may be decreased accordingly.

The method may be provided with the following: (i) the assigning of the plurality of sample containers to the plurality of target devices further comprises providing target device queue status data by processing the target device workload state for at least some target devices from the plurality of target devices, the target device queue status data providing an indirect performance indicator for the target device and being indicative of at least a device identification of the target device and the target device workload state; and (ii) the providing of the plurality of sample containers to the plurality of target devices further comprises controlling a work flow for the at least some target devices in the laboratory system in dependence on the target device queue status data.

The target device workload state is determined in dependence on or responsive to the present number of sample containers assigned to the target device (resource target device state) and the output of sample containers per time by the target device (output flow). Thus, the target device workload state may provide for indirect information about the performance of the target device which in this embodiment is represented by the target device queue status or state, the status of the queue of sample containers assigned to the target device being (indirectly) related to the target device workload state (i.e. the parameters processed for determining the target device workload state). For the plurality of sample containers and target devices workflow can be controlled and managed by taking into account the target device queue status. For example, a target device workload state being indicative of high capacity for handling sample containers can be indicative of a target device queue status with (only) a small number of queued sample containers. Contrary, a target device workload state indicating low capacity for handling sample containers can be (indirectly) indicative of having presently a bigger queue of sample containers for the target device.

The controlling of the work flow may further comprise at least one of the following: (i) disabling a target device from the plurality of target devices, thereby, preventing assignment of a sample container to the disabled target device in a first work flow status of the laboratory system; and (ii) enabling a target device from the plurality of target devices, thereby, allowing assignment of a sample container to the enabled target device in a second work flow status of the laboratory system. Based on the target device queue status data and/or the target device workload state a target device state referring, for example, to "disabling" and "enabling" may be defined and controlled in operation of the laboratory system. In case of the target device workload state and/or the target device queue status data indicating low capacity for handling sample containers, the target device may be disabled. If a target device is disabled before, it may be enabled in response to the target device workload state and/or the target device queue status data indicating high capacity for handling sample containers and small queue status, respectively.

The controlling of the work flow may further comprise the following: providing a target device workload state value indicative of the target device workload state; providing a workload state threshold value. Further, at least one of the following is provided: (i) disabling the target device if the target device workload state value is above the workload state threshold value; and (ii) enabling the target device if the target device workload state value is equal to or below the workload state threshold value. In this embodiment disabling/enabling of the target device is conducted in dependence on a workload state threshold value.

The plurality of laboratory devices providing for the plurality of target devices may comprise one or more laboratory devices from the following group of laboratory devices: a pre-analysis laboratory device configured to perform a pre-analytical task; an analysis laboratory device configured to perform an analytical task for the sample; a post-analysis laboratory device configured to perform post-analytical task; a sample transport device or system configured for sample container transport; a sorter device configured for sample container sorting; and a storage device configured to store one or more sample containers.

With respect to the laboratory system the different embodiments disclosed regarding the method for operating the laboratory system above may apply mutatis mutandis.

DESCRIPTION OF FURTHER EMBODIMENTS

Figure 2:
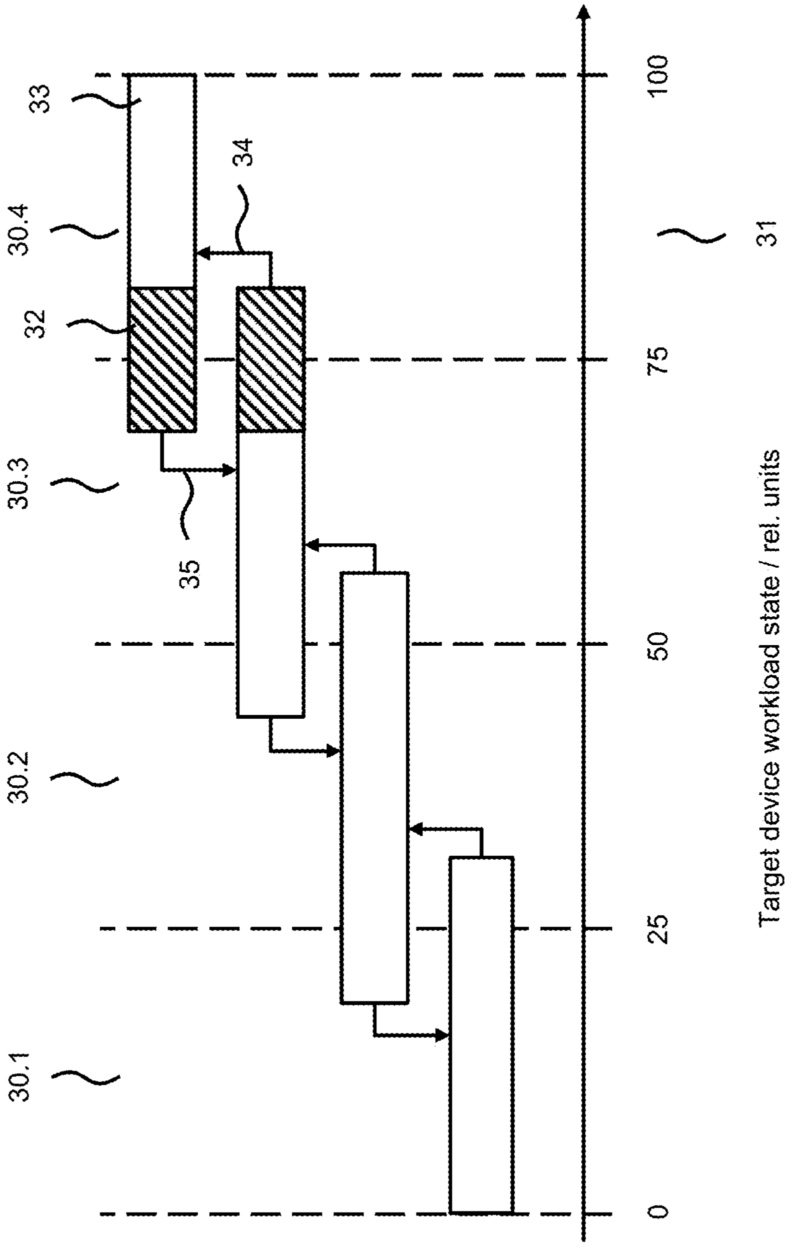

Following, further embodiments are described. Reference is made to figures. In the figures, show:

FIG. 1 a schematic representation of a laboratory system having a plurality of laboratory devices providing for some target devices; and FIG. 2 a schematic representation of a plurality of sub-ranges assigned to a total range of a target device workload state, the sub-ranges being provided with non-overlapping and overlapping ranges.

FIG. 1 shows a schematic representation of a laboratory system comprising a plurality of sample containers 1 which are configured to contain a sample to be processed or handled for at least one of pre-analysis, analysis, and post-analysis in the laboratory system. The plurality of sample containers 1, in the embodiment shown, is provided in an arrival station or device 2. The plurality of sample containers 1 is transported to a plurality of analyzers 3 by means of transport device or system 4. Transport of the plurality of sample containers 1 to the plurality of laboratory devices 3 may be conducted according to a workflow management which is implemented by a control device 5 functionally connected at least to the arrival device 2, and the transport device 4. Optionally, the control device 5 may also be functionally connected to at least some analyzers from the plurality of analyzers 3. The control device 5 may be implemented, at least in part, by one or more software applications running on one or more processors connectable with a data storage device.

After processing by one or more of the analyzers 3, the sample container may be provided to an output station 6 which may also be functionally connected to the control device 5.

In the embodiment shown, the arrival station 2, the output station, the transport device 4 and the plurality of analyzers 3 may provide for a plurality of laboratory devices which may also be referred to as target devices each being configured to handle or process one or more of the sample containers 1 in operation of the laboratory system. In an alternative embodiment one or more of such devices or stations may not be part of the plurality of target devices.

For example, the arrival device 2 is configured to receive the plurality of sample containers 1 and to provide the sample containers 1 to the transport device 4. The transport device 4 is configured to conduct the task of transporting the sample containers 1 to the different analyzers 3. Thus, the task conducted by the transport device 3 is transporting. The analyzers 3 are configured to conduct one or more tasks such as at least one of pre-analytical, analytical and post-analytical task with respect to samples received in the plurality of sample containers 1.

The control device 5 is configured to control assignment of the sample containers 1 to the different target devices which, after receiving a sample container, will accomplish a task related to at least one of the sample container and the sample received in the sample container. In an embodiment, the control device 5 may be configured to control assignment of the sample containers 1 to the plurality of analyzers 3 only, but controlling operation of the arrival station 2 and the transport device 4 for providing the sample containers 1 according to the assignment determined to the plurality of analyzers 3. For example, assigning a sample container to one of the analyzers will mean that such sample container is to be transported from the analyzer by the transport device 4 in the laboratory system. Further, the analyzer receiving the assigned sample container will conduct one of pre-analysis and analysis of the sample received in the assigned sample container.

Following, an embodiment for operating the laboratory system shown in FIG. 1 is described. In operation of the laboratory system, the plurality of sample containers 1 is (individually) assigned to the target devices in dependence on a target device workload state which in operation is determined one or more times for some or all of the target devices, specifically the plurality of analyzers 3 individually.

A target device workload state is determined for the plurality of target devices. The target device workload state, for example, can determined by the control device 5 or some data processing device (not shown) connectable to the control device 5 for data transmission and can be for example a numerical value being in a range between a first range limit indicative of a first capacity for handling sample containers and a second range limit indicative a second capacity for sample containers. The second capacity is a higher capacity than the first capacity for handling sample containers. Thus, the target device for which the target device workload state determined is indicating a high capacity for handling sample containers will most likely be able to fulfill some task provided by such target device faster than a different target device having assigned a target device workload state indicative of lower capacity.

In an embodiment, the target device workload state of the target device i ($WLS_{TD\ i}$) (i=1, 2, . . . ) is determined as follows:

$$WLS_{TD\,i} = \frac{R_i}{R_{init}} \cdot (k_{SC\,i})^w \cdot 100$$

wherein $R_i$ is a resource target device state of the target device, $R_{init}$ is an initial resource target device state of the target device, and $(k_{SC\ i})^w$ is an output flow of the target device provided with the weighting factor w. The resource target device state $R_i$ is indicative of a present number of sample containers assigned to the target device i. The output flow of the target device $$k_{SC\,i}^w$$

provided with the weighting factor w is indicative of an output of sample containers per time (period or range) by the target device i. $R_{init}$ is indicative of a starting number of sample containers assigned to the target device i.

In an embodiment, the throughput or output flow factor $k_{SC\ i}$ may be defined by the count of sample containers that actually left the system at a target device (after processing the sample container containing the sample) divided by the number of sample containers that were expected to leave:

$$k_{SC\,i} = \frac{\sum sc_i}{\sum sc_{exp,\,i}},$$

wherein $\Sigma SC_i$ is the number of sample containers left at the target device i, and $\Sigma SC_{exp,i}$ is the number of sample containers expected to leave at the target device i. In order to calculate a moving average value, the two counts $\Sigma SC_i$ and $\Sigma SC_{exp,i}$ may be represented as a vector, and the sum of all vector entries may be taken for determining the sample container throughput factor.

In view of having applied different weighting factor w for different priorities, change of the throughput or output flow factor $k_{SC\ i}$ will have different impact in the target device workload state for different priorities.

If the target devices processes as many sample containers as it is able to do, i.e. operating according to expectation, the above equation approaches 1. It refers to the sum over time, so some past performance of the target device is considered, e.g. a period of last 10 minutes. If no sample containers are available for processing, the queue of the target device is empty. In such case the value is set to 1 as it is assumed that the target device would have been able to process sample containers if such sample containers would be provided to the target device.

With respect to the numbers $SC_i$ and $SC_{exp,\ i}$, one or more of the following rules may be applied.

$SC_i$ is may be increased when a sample container is handed over to a connected device component or is processed by an in-situ device at the target device i.

For increasing $SC_{exp,\ i}$ one or more of the following rules may be applied: (i) In case a sample container enters a static sample container output queue, $SC_{exp,\ i}$ is decreased (for example, to a minimum of 0) when the sample container entering the static sample container output queue is re-routed and already reached the static sample container output queue. (ii) In case a sample container is assigned to the target device i, $SC_{exp,\ i}$ is decreased (for example, to a minimum of 0) when the sample container assigned to the target device i is re-routed. (iii) In case a sample container reaches a first position in the TSIF, which is the first position after the cache field, the $SC_{exp,\ i}$ is not decreased. Applying rules (ii) and/or (iii) will increase $SC_{exp,\ i}$. It leads to not depend on the static queue especially its design or layout.

In case the target device workload state is determined by the control device 5, the control device 5 may receive data indicative of the above parameters from the target devices directly, for example, the analyzers 3 and the arrival station 2. At least in part, software application(s) of the control device 5 may be assigned to some middleware. The term "middleware" can be used for software that enables communication and management of data in a distributed application system of the laboratory system.

Based on the target device workload state determined individually for some or all target devices from the plurality of target devices, the plurality of sample containers 1 will be assigned to the plurality of target devices, for example to the analyzers 3, in operation of the laboratory system. In an example, a sample container to which some specific task has to be applied, such specific task being made available by at least two of the plurality of analyzers 3, may be assigned to the analyzer from the at least two analyzers for which the target device workload state indicates higher capacity for handling the sample container. Thus, based on the target device workload state load balancing may be conducted for the plurality of sample containers 1 to be handled in the laboratory system.

Handling of the plurality of sample containers 1 in the laboratory system may be conducted with different level of priority. For example, a first priority may be referred to as "normal priority". A second level of priority may be referred to as "urgent priority". The latter is giving indication about urgency for conducting handling of a sample container in the laboratory system. For some or all of the plurality of analyzers 3 the target device workload state may be determined for both "normal priority" and "urgent priority". Thus, at least two target device workload states will be assigned to the analyzers 3.

The target device workload states determined for the different levels of priority may be equal or different. If a sample container is to be processed according to the level of priority "normal priority", assignment of the sample container to the plurality of analyzers 3 will be controlled based on the target device workload state determined for the level of priority "normal priority". Contrary, if a different sample container needs to be processed in the laboratory system according to the level of priority "urgent priority", assignment of the different sample container for conducting the necessary task for analysis will be controlled based on the target device workload states determined for the level of priority "urgent priority". In conclusion, actual assignment of a sample container to some can depend on the level of priority for processing of the sample container.

Referring to FIG. 2 a schematic representation of a plurality of sub-ranges 30.1, . . . , 30.4 is depicted. The plurality of sub-ranges 30.1, . . . , 30.4 together make up a total range 31 from 0 to 100 (rel. units) allowed for the target device workload state for some target device. There are overlapping ranges 32 in which adjacent or neighboring sub-ranges from the plurality of sub-ranges 30.1, . . . , 30.4 are overlapping. In a non-overlapping range 33 there is no overlapping between adjacent or neighboring sub-ranges. In an example, the plurality of sub-ranges 30.1, . . . , 30.4 may be assigned the following target device workload state (percentage): 0 to 30% (30.1), 20 to 55% (30.2, 45 to 80% (30.3), and 70 to 100% (30.4).

In case a present target device workload state ((percentage) value) is determined to be within the non-overlapping range 33 after being determined falling within the overlapping range 32 before (former target device workload state), assignment of sample containers to the target device will be controlled by taking into account the present target device workload state (value) instead of the former target device workload state applied before (transition 34). Similar controlling of the assignment of the sample containers to the target device based on the target device workload state is applied in case of opposite transition 35. While the target device workload state (value) may be updated more often, e.g. every time the resource state changes or the sample container throughput factor is re-calculated, actual assignment of sample containers to the target device will (only) change (change of sub-range) if the target device workload state is determined to be moved from an overlapping range into an non-overlapping range. It will keep the number of changes in assignment of sample containers due to change of target device workload state at a reasonable low level.

The invention claimed is:

1. A method for operating a laboratory system, comprising providing a laboratory system having:

a plurality of sample containers configured to contain a sample to be processed for at least one of pre-analysis and analysis in the laboratory system;

a plurality of laboratory devices providing for a plurality of target devices each configured to handle one or more sample containers from the plurality of sample containers, the one or more sample containers being assigned for handling to the target device in operation of the laboratory system; and a control device configured to at least control assignment of the plurality of sample containers to the plurality of target devices; and assigning the plurality of sample containers to the plurality of target devices in operation of the laboratory system, comprising:

determining a target device workload state for each of the plurality of target devices, the target device workload state being in a range between a first range limit indicative of a first capacity for handling sample containers and a second range limit indicative of a second capacity for handling sample containers, the second capacity being a higher capacity than the first capacity for handling sample containers, and determined according to a metric being proportional to a resource target device state indicative of a present number of sample containers assigned to the target device, and a power of an output flow of the target device, the output flow being indicative of output of sample containers per time by the target device;

assigning the plurality of sample containers to the plurality of target devices according to the target device workload states; and providing the plurality of sample containers to the plurality of target devices for handling according to the assignment to provide improved efficiency in handling of the sample containers in the laboratory system, wherein providing the plurality of sample containers according to the assignment comprises transporting, with a transport device that is connected to the control device, a sample container along a physical path to a corresponding analyzer device configured to perform a pre-analytical, analytical, or post-analytical task on the corresponding sample.

2. The method of claim 1, wherein the metric is proportional to the output flow of the target device raised to the power of a weighting factor, the weighting factor weighting the output flow of the target device for determining the target device workload state.

3. The method of claim 1, wherein the metric is inversely proportional to an initial resource target device state indicative of a starting number of sample containers assigned to the target device.

4. The method of claim 1, wherein the target device workload state of the target device i ($WLS_{TD\,i}$) is determined as follows:

$$WLS_{TDi} = \frac{R_i}{R_{init}} k_{SC\,i}^{w} \cdot 100$$

wherein $R_i$ is the resource target device state of the target device, $R_{init}$ is the initial resource target device state of the target device, and $k_{SC\,i}^{\;w}$ is the output flow of the target device provided with the weighting factor w.

5. The method of claim 1, further comprising determining an updated target device workload state for the target device in response to at least one of the following: updating the resource target device state of the target device, and recalculating output flow of the target device.

6. The method of claim 1, further comprising providing a plurality of sub-ranges for a first range of the target device workload state for a first target device, wherein an overlapping range is provided for adjacent sub-ranges from the plurality of sub-ranges in which the adjacent sub-ranges are overlapping;

determining a first target device workload state for the first target device, the first target device workload state being in a non-overlapping range of a first sub-range in which the first subrange is not overlapping with a second sub-range adjacent to the first sub-range;

assigning the plurality of sample containers to the first target device according to the first target device workload state;

determining a second target device workload state for the first target device, the second target device workload state being different from the first target device workload state and being in the overlapping range in which the first sub-range and the second sub-range are overlapping;

continuing with assigning the plurality of sample containers to the first target device according to the first target device workload state;

determining a third target device workload state for the first target device, the third target device workload state being different from both the first and the second target device workload states and being in a non-overlapping range of the second sub-range in which the first sub-range and the second sub-range are not overlapping; and assigning the plurality of sample containers to the first target device according to the second target device workload state.

7. The method of claim 1, further comprising providing first priority data indicative of a first priority for handling a first sample container from the plurality of sample containers;

providing second priority data indicative of a second priority for handling the first sample container, the second priority being indicative of lower urgency for handling the first sample container in operation than the first priority;

determining a first priority target device workload state for the first sample container according to the first priority;

determining a second priority target device workload state for the first sample container according to the second priority;

selecting one of the first priority target device workload state and the second priority target device workload state; and assigning the target device workload state selected to the first sample container.

8. The method of claim 1, wherein the assigning of the plurality of sample containers to the plurality of target devices further comprises providing target device queue status data by processing the target device workload state for at least some target devices from the plurality of target devices, the target device queue status data providing an indirect performance indicator for the target device and being indicative of at least a device identification of the target device and the target device workload state; and the providing of the plurality of sample containers to the plurality of target devices further comprises controlling a work flow for the at least some target devices in the laboratory system in dependence on the target device queue status data.

9. The method of claim 8, wherein the controlling of the work flow is further comprising at least one of disabling a target device from the plurality of target devices, thereby, preventing assignment of a sample container to the disabled target device in a first work flow status of the laboratory system; and enabling a target device from the plurality of target devices, thereby, allowing assignment of a sample container to the enabled target device in a second work flow status of the laboratory system.

10. The method of claim 9, wherein the controlling of the work flow is further comprising providing a target device workload state value indicative of the target device workload state;

providing a workload state threshold value; and at least one of the following:

disabling the target device if the target device workload state value is above the workload state threshold value; and enabling the target device if the target device workload state value is equal to or below the workload state threshold value.

11. A laboratory system, comprising a plurality of sample containers configured to contain a sample;

a plurality of laboratory devices providing for a plurality of target devices each configured to handle one or more sample containers from the plurality of sample containers, the one or more sample containers being assigned for handling to the target device in operation of the laboratory system; and a control device configured to at least control assignment of the plurality of sample containers to the plurality of target devices;

wherein the laboratory system is configured to process the plurality of sample containers for at least one of pre-analysis and analysis of the sample and further to assign the plurality of sample containers to the plurality of target devices in operation, comprising:

determining a target device workload state for each of the plurality of target devices, the target device workload state being in a range between a first range limit indicative of a first capacity for handling sample containers and a second range limit indicative a second capacity for handling sample containers, the second capacity being a higher capacity than the first capacity for handling sample containers, and determined according to a metric being proportional to a resource target device state indicative of a present number of sample containers assigned to the target device, and a power of an output flow of the target device, the output flow being indicative of output of sample containers per time by the target device;

assign the plurality of sample containers to the plurality of target devices according to the target device workload states; and provide the plurality of sample containers to the plurality of target devices for handling according to the assignment to provide improved efficiency in handling of the sample containers in the laboratory system, wherein to provide the plurality of sample containers according to the assignment comprises to transport, with a transport device that is connected to the control device, a sample container along a physical path to a corresponding analyzer device configured to perform a pre-analytical, analytical, or post-analytical task on the corresponding sample.

12. The system of claim 11, wherein the plurality of laboratory devices providing for the plurality of target devices comprise one or more laboratory devices from the following group of laboratory devices:

a pre-analysis laboratory device configured to perform a pre-analytical task;

an analysis laboratory device configured to perform an analytical task for the sample;

a post-analysis laboratory device configured to perform post-analytical task;

a sample transport device configured for sample container transport;

a sorter device configured for sample container sorting; and a storage device configured to store one or more sample containers.

13. The method of claim 1, wherein transporting the sample container comprises transporting the sample container on a transportation surface of the transport device to the corresponding analyzer device according to the assignment.

* * * * *